(12) United States Patent
Kim et al.

(10) Patent No.: US 8,420,685 B2
(45) Date of Patent: Apr. 16, 2013

(54) 2-PYRIDYL SUBSTITUTED IMIDAZOLES AS ALK5 AND/OR ALK4 INHIBITORS

(75) Inventors: Dae-Kee Kim, Seoul (KR); Yung-Jue Bang, Seoul (KR); Hun-Taek Kim, Seoul (KR); Ii-Sang Cho, Seoul (KR); Myoung-Soon Park, Gyeonggi-do (KR); Young Jae An, Seoul (KR); Joon Hun Choi, Seoul (KR)

(73) Assignees: SK Chemicals Co., Ltd., Suwon (KR); Ewha University Industry Collaboration Foundation, Seoul (KR)

( * ) Notice: Subject to any disclaimer, the term of this patent is extended or adjusted under 35 U.S.C. 154(b) by 0 days.

(21) Appl. No.: 12/155,989

(22) Filed: Jun. 12, 2008

(65) Prior Publication Data
US 2008/0319022 A1 Dec. 25, 2008

Related U.S. Application Data

(63) Continuation-in-part of application No. 10/983,227, filed on Nov. 8, 2004, now Pat. No. 7,407,958.

(30) Foreign Application Priority Data

Apr. 21, 2004 (KR) .................. 2004-27591

(51) Int. Cl.
*A61K 31/415* (2006.01)
(52) U.S. Cl.
USPC ............... 514/397; 546/274.1; 548/335.1; 549/398; 549/464

(58) Field of Classification Search .............. 514/397; 546/274.1; 548/335.1; 549/398, 464
See application file for complete search history.

(56) References Cited

FOREIGN PATENT DOCUMENTS
WO WO 2005/103028 * 11/2005

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*

* cited by examiner

*Primary Examiner* — Douglas M Willis
(74) *Attorney, Agent, or Firm* — William E. Beaumont

(57) ABSTRACT

A compound of the formula:

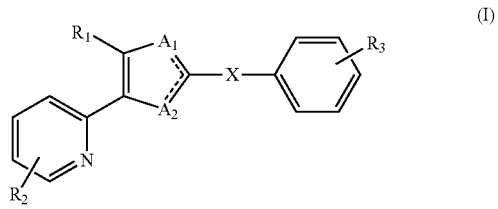

Wherein $A_1$, $A_2$, X, $R_2$ and R3 are as defined herein, or a composition containing the same, which compound is useful in treating renal-, liver- or pulmonary fibrosis.

9 Claims, No Drawings

2-PYRIDYL SUBSTITUTED IMIDAZOLES AS ALK5 AND/OR ALK4 INHIBITORS

CROSS-REFERENCE TO RELATED APPLICATIONS

This application is a Continuation-In-Part (CIP) application of application Ser. No. 10/983,227, filed Nov. 8, 2004 now U.S. Pat. No. 7,407,958, claiming priority of Korean Application No. 10-2004-0027591, filed on Apr. 21, 2004, the disclosure of which is incorporated fully herein by reference.

FIELD OF THE INVENTION

The present invention relates to 2-pyridyl-substituted imidazoles which are inhibitors of the transforming growth factor-β (TGF-β) type I receptor (ALK5) and/or the activin type I receptor (ALK4), methods for their preparation, and their use in medicine, specifically in the treatment and prevention of a disease state mediated by these receptors.

DESCRIPTION OF BACKGROUND

TGF-β denotes a family of proteins, TGF-β1, TGF-β2 and TGF-β3, which are pleiotropic modulators of cell proliferation and differentiation, wound healing, extracellular matrix production and immunosuppression. Other members of this superfamily include activins, inhibins, bone morphogenetic proteins, growth and differentiation factors and Müllerian inhibiting substance.

TGF-β1 transduces signals through two highly conserved single transmembrane serine/threonine kinases, the type I (ALK5) and type II TGF-β receptors. Upon ligand induced oligomerization, the type II receptor hyperphosphorylates serine/threonine residues in the GS region of the ALK5, which leads to activation of the ALK5 by creating a binding site for Smad proteins. The activated ALK5 in turn phosphorylates Smad2 and Smad3 proteins at the C-terminal SSXS-motif thereby causing their dissociation from the receptor and heteromeric complex formation with Smad4. Smad complexes translocate to the nucleus, assemble with specific DNA-binding co-factors and co-modulators to finally activate transcription of extracellular matrix components and inhibitors of matrix-degrading proteases.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

Numerous experimental animal studies demonstrate an association between glomerular expression of TGF-β and fibrosis, including the Thy-1 rat model of proliferative glomerulonephritis, anti-GBM glomerulonephritis in rabbits, and the 5/6 nephrectomy rat model of focal segmental glomerulosclerosis, as has been reviewed recently (e.g., Bitzer, M. et al., *Kidney Blood Press. Res.* 21:1-12 (1998)). Neutralizing antibody to TGF-β improves glomerular histology in the Thy-1 nephritis model (e.g., Border, W. A. et al., *Nature* 346: 371-374 (1990)).

Hyperglycemic conditions increase TGF-β mRNA and protein synthesis in both murine proximal tubule cells and human mesangial cells (e.g., Wahab, N. A. et al., *Biochem. J.* 316:985-992 (1996); Rocco, M. V. et al., *Kidney Int.* 41: 107-114 (1992)). Diabetic patients with early kidney disease show increased accumulation of TGF-β mRNA and protein within the glomerulus (e.g., Yoshioka, K. et al., *Lab. Invest.* 68: 154-163 (1993)). In kidneys with chronic renal interstitial fibrosis, the hallmarks are thickened tubular basement membranes and an expanded interstitial compartment, with interstitial fibrosis characterized by an increase in collagens I, III, V, VII, and fibronectin (e.g., Eddy, A. A., *J. Am. Soc. Nephrol.* 7: 2495-2508 (1996)).

TGF-β gene expression and protein production are increased in a variety of animal models of pulmonary fibrosis including bleomycin, silica, asbestos, and radiation (e.g., Phan, S. H. and Kunkel, S. L., *Exp. Lung Res.* 18: 29-43 (1992); Williams, A. O. et al., *Am. J. Pathol.* 142: 1831-1840 (1993); Rube, C. E. et al., *Int. J. Radiat. Oncol. Biol. Phys.* 47: 1033-1042 (2000)). Coincident increase in TGF-β1 protein and collagen gene expression in adjacent tissue slices from idiopathic pulmonary fibrosis is observed in human pulmonary fibrotic disease (e.g., Broekelmann, T. J. et al., *Proc. Natl. Acad. Sci. USA* 88:6642-646 (1991)). Increased TGF-β production has been documented in patients with sarcoidosis, pneumoconiosis, asbestosis, and radiation-induced fibrosis (e.g., Khalil, N. et al., *Am. J. Respir. Cell. Mol. Biol.* 14:131-138 (1996); Jagirdar, J. et al., *Environ. Health Perspect.* 105: 1197-1203 (1997)). Anti-TGF-β antibodies and TGF-β-soluble receptors could partially inhibit fibrosis in bleomycin-induced lung fibrosis rodent models (e.g., Giri, S. N. et al., *Thorax* 48: 959-966 (1993); Wang, Q. et al., *Thorax* 54: 805-812 (1999)). Tobacco smoke has been implicated as one of the most important factors that can cause small airway disease followed by chronic obstructive pulmonary disease (COPD) (e.g., Wright, J. M. et al., *Am. Rev. Respir. Dis.* 146: 240-262 (1992)). COPD is a slowly progressive and irreversible disorder characterized by the functional abnormality of airway obstruction. TGF-β has been hypothesized to be involved in airway remodeling found in chronic airway inflammatory disorders such as COPD (e.g., Takizawa, H. *Int. J. Mol. Med.* 1: 367-378 (1998); Ning, W. et al., *Proc. Natl. Acad. Sci. USA* 101:14895-14900 (2004)).

Hepatic stellate cells (HSC) are the major source of extracellular matrix proteins in hepatic fibrosis. Extracellular matrix production by activated hepatic stellate cells is markedly increased through the action of TGF-β1 (e.g., Friedman, S. L., *Prog. Liver Dis.* 14: 101-130 (1996); Pietrangelo, A., *Semin. Liver Dis.* 16:13-30 (1996)). Transgenic mice that overexpress TGF-β1 in the liver develop hepatic fibrosis as well as extrahepatic pathologies such as renal fibrosis (e.g., Sanderson, N. et al., *Proc. Natl. Acad. Sci. USA* 92:2572-2576 (1995)).

TGF-β1 and its receptors are overexpressed in injured blood vessels and in fibroproliferative vascular lesions leading to overproduction of extracellular matrix (e.g., Saltis, J. et al., *Clin. Exp. Pharmacol. Physiol.* 23: 193-200 (1996); McCaffrey, T. A. et al., *J. Clin. Invest.* 96: 2667-2675 (1995)).

Anti-TGF-β antibodies reduce scar formation and improve the cytoarchitecture of the neodermis in rats (e.g., Shah, M., *J. Cell. Sci.* 108: 985-1002 (1995)), improve healing of corneal wounds in rabbits (e.g., Moller-Pedersen, T., *Curr. Eye Res.* 17:736-747 (1998)), and accelerate wound healing of gastric ulcers in rats (e.g., Ernst, H., *Gut* 39: 172-175 (1996)).

Radiation fibrosis is a frequent sequel of therapeutic or accidental radiation overexposure in normal human tissues. TGF-β1 plays a central role in the initiation, development, and persistence of radiation fibrosis, as has been reviewed recently (e.g., Martin, M. et al., *Int. J. Radiat. Oncol. Biol. Phys.* 47:277-290 (2000)).

Organ transplantation is complicated in many instances by chronic rejection and for some organs such as the kidney, it is the major forms of graft loss. In human patients, chronic rejection of lung and kidney transplants is associated with increased expression of TGF-β within the tissue (e.g., El-Gamel, A. et al., *Eur. J. Cardiothorac. Surg.* 13: 424-430 (1998); Shihab, F. S. et al., *J. Am. Soc. Nephrol.* 6:286-294 (1995)).

TGF-β is implicated in peritoneal adhesions (e.g., Saed, G. M. et al., *Wound Repair Regeneration* 7: 504-510 (1999)). The peritoneal and sub-dermal fibrotic adhesions could be prevented by inhibitors of ALK5 and/or ALK4.

The tumor cells and the stromal cells within the tumors in late stages of various cancers generally overexpress TGF-β. This leads to stimulation of angiogenesis and cell motility, suppression of the immune system, and increased interaction of tumor cells with the extracellular matrix (e.g., Hojo, M. et al., *Nature* 397: 530-534 (1999)). Consequently, the tumor cells become more invasive and metastasize to distant organs (e.g., Maehara, Y. et al., *J. Clin. Oncol.* 17: 607-14 (1999); Picon, A. et al., *Cancer Epidemiol. Biomarkers Prev.* 7:497-504 (1998)).

Plasminogen activator inhibitor-1 (PAI-1) is the major physiological inhibitor of both tissue-type plasminogen activator and urokinase-type plasminogen activator. Elevated levels of PAI-1 are associated with thrombosis and vascular disease, suggesting that high plasma PAI-1 may promote a hypercoagulable state by disrupting the natural balance between fibrinolysis and coagulation (e.g., Vaughan, D. E., *J. Invest. Med.* 46: 370-376 (1998)). It is known that TGF-β stimulates the expression of PAI-1 (e.g., Dennler, S. et al., *EMBO J.* 17: 3091-3100 (1998)). Accordingly, inhibition of the production of PAI-1 with an inhibitor of the TGF-β signaling pathway could produce a novel fibrinolytic therapy.

Activin signaling and overexpression of activin is linked to pathological disorders that involve extracellular matrix accumulation and fibrosis (e.g., Matsuse, T. et al., *Am. J. Respir. Cell Mol. Biol.* 13:17-24 (1995); Inoue, S. et al., *Biochem. Biophys. Res. Comm.* 205:441-448 (1994); Matsuse, T. et al., *Am. J. Pathol.* 148:707-713 (1996); De Bleser et al., *Hepatology* 26:905-912 (1997); Pawlowski, J. E., et al., *J. Clin. Invest.* 100:639-648 (1997); Sugiyama, M. et al., *Gastroenterology* 114:550-558 (1998); Munz, B. et al., *EMBO J.* 18:5205-5215 (1999)), inflammatory responses (e.g., Rosendahl, A. et al., *Am. J. Respir. Cell Mol. Biol.* 25:60-68 (2001); cachexia or wasting (Matzuk, M. M. et al., *Proc. Natl. Acd. Sci. USA* 91:8817-8821 (1994); Coerver, K. A. et al., *Mol. Endocrinol.* 10:534-543 (1996); Cipriano, S. C. et al., *Endocrinology* 141:2319-2327 (2000)), diseases or pathological responses in the central nervous system (e.g., Logan, A. et al., *Eur. J. Neurosci.* 11:2367-2374 (1999); Logan, A. et al., *Exp. Neurol.* 159:504-510 (1999); Masliah, E. et al., *Neurochem. Int.* 39:393-400 (2001); De Groot, C. J. A. et al., *J. Neuropathol. Exp. Neurol.* 58:174-187 (1999); John, G. R. et al., *Nat. Med.* 8:1115-1121 (2002)) and hypertension (e.g., Dahly, A. J. et al., *Am. J. Physiol. Regul. Integr. Comp. Physiol.* 283: R757-767 (2002)). Studies have shown that TGF-β and activin can act synergistically to induce extracellular matrix production (e.g., Sugiyama, M. et al., *Gastroenterology* 114; 550-558 (1998)).

WO 00/61576 and US 2003/0149277 A1 disclose triarylimidazole derivatives and their use as ALK5 inhibitors. WO 01/62756 A1 discloses pyridinylimidazole derivatives and their use as ALK5 inhibitors. WO 02/055077 A1 discloses use of imidazolyl cyclic acetal derivatives as ALK5 inhibitors. And, also, WO 03/087304 A2 discloses tri-substituted heteroaryls and their use as ALK5 and/or ALK4 inhibitors.

SUMMARY OF THE INVENTION

Surprisingly, it has now been discovered that a class of 2-pyridyl-substituted imidazoles function as potent and selective inhibitors of ALK5 and/or ALK4 and therefore, have utility in the treatment and prevention of various disease states mediated by ALK5 and/or ALK4, such as glomerulonephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Alzheimer's disease, Raynaud's syndrome, fibrotic cancers, tumor metastasis growth, radiation-induced fibrosis, and thrombosis.

DETAILED DESCRIPTION OF THE PREFERRED EMBODIMENTS

In one embodiment of the present invention, there is provided a compound of formula (I) or a pharmaceutically acceptable salt thereof:

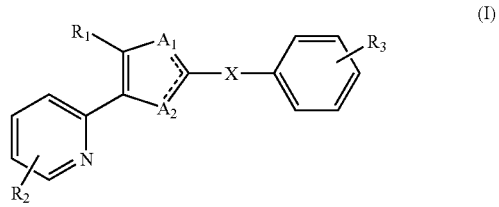

wherein $R_1$ is phenyl or pyridyl fused with an aromatic or non-aromatic cyclic ring of 5-7 members wherein said cyclic ring optionally contains up to three heteroatoms, independently selected from the group consisting of O and S; or $R_1$ is phenyl or pyridyl optionally substituted by halo, OH, —O—$C_{1-6}$alkyl, —S—$C_{1-6}$alkyl, $C_{1-6}$alkyl, $C_{1-6}$haloalkyl, cyano, phenyl or =O;

$R_2$ is H, OH, —O—$C_{1-6}$alkyl, —S—$C_{1-6}$alkyl, $C_{1-6}$alkyl, phenyl, $C_{1-6}$haloalkyl, $NH_2$, $NH(CH_2)_n$-Ph, NH—$C_{1-6}$alkyl, halo, CN, $NO_2$, CONHR or $SO_2NHR$, wherein R is H or $C_1$alkyl, and n is 0, 1, 2, or 3;

$R_3$ is H, $C_{1-6}$alkyl, $C_{3-7}$cycloalkyl, —$(CH_2)_p$—$NO_2$, —$(CH_2)_p$—$NR_4R_5$, —$(CH_2)_p$—CHO, —$(CH_2)_p$—CONHOH, —$(CH_2)_p$—CN, —$(CH_2)_p$—$CO_2H$, —$(CH_2)_p$—$CO_2R_4$, —$(CH_2)_p$—$CONR_4R_5$, —$(CH_2)_p$-tetrazole, —$(CH_2)_p$—$COR_4$, —$(CH_2)_q$—$(OR_6)_2$, —$(CH_2)_p$—$OR_4$, —(CH$_2$)$_p$—CH=CH—CN, —(CH$_2$)$_p$—CH=CH—CO$_2$H, —(CH$_2$)$_p$—CH=CH—CO$_2$R$_4$, —(CH$_2$)$_p$—CH=CH—CONR$_4$R$_5$, —(CH$_2$)$_p$—NHCOR$_4$, —(CH$_2$)$_p$—NHCO$_2$R$_4$, —(CH$_2$)$_p$—CONHSO$_2$R$_4$, —(CH$_2$)$_p$—NHSO$_2$R$_4$ or —(CH$_2$)$_p$—CH=CH-tetrazole;

R$_4$ and R$_5$ are independently H or C$_{1-6}$alkyl;

R$_6$ is C$_{1-6}$alkyl;

p is 0, 1, 2, 3, or 4;

q is 1, 2, 3, or 4;

X is C$_{1-10}$alkylene, C$_{2-10}$alkenylene, or C$_{2-10}$alkynylene;

one of A$_1$ and A$_2$ is N and the other is NR$_7$; and

R$_7$ is H, OH, C$_{1-6}$alkyl, or C$_{3-7}$cycloalkyl.

As used herein, the double bond indicated by the dotted lines of formula (I), represent the possible tautomeric ring forms of the compounds falling within the scope of this invention, the double bond being to the unsubstituted nitrogen.

Preferably, R$_1$ is phenyl fused with an aromatic or non-aromatic cyclic ring of 5-7 members wherein said cyclic ring optionally contains up to two heteroatoms, independently selected from O and S; or R$_1$ is phenyl optionally substituted by halo, OH, —O—C$_{1-6}$alkyl, —S—C$_{1-6}$alkyl, C$_{1-6}$alkyl, C$_{1-6}$haloalkyl, cyano, phenyl or =O. For example, R$_1$ represents benzo[1,3]dioxolyl, 2,3-dihydrobenzo[1,4]dioxinyl, benzoxazolyl, benzothiazolyl, benzo[1,2,5]oxadiazolyl, benzo[1,2,5]thiadiazolyl, quinoxalinyl, dihydrobenzofuranyl, benzimidazolyl, C$_{1-6}$-benzimidazolyl, [1,2,4]triazolo[1,5-a]pyridyl, benzo[1,4]oxazinyl-3-one, benzoxazolyl-2-one or benzo[1,4]oxazinyl.

Preferably, R$_2$ is other than H. When R$_2$ is other than H, it is preferably positioned ortho to the nitrogen of the pyridyl ring. R$_2$ is preferably C$_{1-4}$ alkyl.

Preferably, R$_3$ is —(CH$_2$)$_p$—CONHOH, —(CH$_2$)$_p$—CN, —(CH$_2$)$_p$—CO$_2$H, —(CH$_2$)$_p$—CONR$_4$R$_5$, or —(CH$_2$)$_p$-tetrazole.

Preferably, R$_4$ and R$_5$ are independently H or C$_{1-3}$alkyl.

Preferably, p is 0, 1, or 2.

Preferably, X is C$_{1-6}$alkylene.

Preferably, one of A$_1$ and A$_2$ is N and the other is NR$_7$, wherein R$_7$ is H.

Specific compounds of the invention which may be mentioned include the following and pharmaceutically acceptable salts thereof:

4-((4-(benzo[1,3]dioxol-5-yl)-5-(pyridin-2-yl)-1(3)H-imidazol-2-yl)methyl)benzonitrile;

4-((4-(benzo[1,3]dioxol-5-yl)-5-(pyridin-2-yl)-1(3)H-imidazol-2-yl)methyl)benzamide;

4-((4-(benzo[1,3]dioxol-5-yl)-5-(6-methylpyridin-2-yl)-1(3)H-imidazol-2-yl)methyl)benzonitrile;

4-((4-(benzo[1,3]dioxol-5-yl)-5-(6-methylpyridin-2-yl)-1(3)H-imidazol-2-yl)methyl)benzamide;

3-((4-(benzo[1,3]dioxol-5-yl)-5-(6-methylpyridin-2-yl)-1(3)H-imidazol-2-yl)methyl)benzonitrile;

3-((4-(benzo[1,3]dioxol-5-yl)-5-(6-methylpyridin-2-yl)-1(3)H-imidazol-2-yl)methyl)benzamide;

4-(2-(4-(benzo[1,3]dioxol-5-yl)-5-(pyridin-2-yl)-1(3)H-imidazol-2-yl)ethyl)benzonitrile;

4-(2-(4-(benzo[1,3]dioxol-5-yl)-5-(pyridin-2-yl)-1(3)H-imidazol-2-yl)ethyl)benzamide;

4-(2-(4-(benzo[1,3]dioxol-5-yl)-5-(6-methylpyridin-2-yl)-1(3)H-imidazol-2-yl)ethyl)benzonitrile;

4-(2-(4-(benzo[1,3]dioxol-5-yl)-5-(6-methylpyridin-2-yl)-1(3)H-imidazol-2-yl)ethyl)benzamide;

4-(3-(4-(benzo[1,3]dioxol-5-yl)-5-(pyridin-2-yl)-1(3)H-imidazol-2-yl)propyl)benzonitrile;

4-(3-(4-(benzo[1,3]dioxol-5-yl)-5-(pyridin-2-yl)-1(3)H-imidazol-2-yl)propyl)benzamide;

4-(3-(4-(benzo[1,3]dioxol-5-yl)-5-(6-methylpyridin-2-yl)-1(3)H-imidazol-2-yl)propyl)benzonitrile;

4-(3-(4-(benzo[1,3]dioxol-5-yl)-5-(6-methylpyridin-2-yl)-1(3)H-imidazol-2-yl)propyl)benzamide;

4-((4-(2,3,4a,8a-tetrahydrobenzo[b][1,4]dioxin-7-yl)-5-(pyridin-2-yl)-1(3)H-imidazol-2-yl)methyl)benzamide;

4-((4-(2,3,4a,8a-tetrahydrobenzo[b][1,4]dioxin-7-yl)-5-(6-methylpyridin-2-yl)-1(3)H-imidazol-2-yl)methyl)benzamide;

4-((4-(3-methoxyphenyl)-5-(pyridin-2-yl)-1H-imidazol-2-yl)methyl)benzonitrile;

4-((4-(3-methoxyphenyl)-5-(pyridine-2-yl)-1H-imidazol-2-yl)methyl)benzamide;

4-((4-(3-methoxyphenyl)-5-(6-methylpyridin-2-yl)-1H-imidazol-2-yl)methyl)benzonitrile;

4-((4-(3-methoxyphenyl)-5-(6-methylpyridin-2-yl)-1H-imidazol-2-yl)methyl)benzamide;

4-((4-(3-fluorophenyl)-5-(pyridine-2-yl)-1H-imidazol-2-yl)methyl)benzonitrile;

4-((4-(3-fluorophenyl)-5-(pyridin-2-yl)-1H-imidazol-2-yl)methyl)benzamide;

4-((4-(3-fluorophenyl)-5-(6-methylpyridin-2-yl)-1H-imidazol-2-yl)methyl)benzonitrile;

4-((4-(3-fluorophenyl)-5-(6-methylpyridin-2-yl)-1H-imidazol-2-yl)methyl)benzamide;

4-((4-(3-fluoro-4-methoxyphenyl)-5-(pyridin-2-yl)-1H-imidazol-2-yl)methyl)benzonitrile;

4-((4-(3-fluoro-4-methoxyphenyl)-5-(pyridin-2-yl)-1H-imidazol-2-yl)methyl)benzamide;

4-((4-(3-fluoro-4-methoxyphenyl)-5-(6-methylpyridin-2-yl)-1H-imidazol-2-yl)methyl)benzonitrile; and 4-((4-(3-fluoro-4-methoxyphenyl)-5-(6-methylpyridin-2-yl)-1H-imidazol-2-yl)methyl)benzamide.

The compounds of the present invention typically are small organic molecules (non-peptide small molecules), generally less than about 1,000 daltons in size. Preferred non-peptide small molecules have molecular weights of less than about 750 daltons, more preferably less than about 500 daltons, and even more preferably less than about 300 daltons.

Compounds of formula (I) may also be supplied in the form of a "prodrug" which is designed to release compound of formula (I) when administered to a subject. Prodrug formed designs are well known in the art, and depend on the substituents contained in compound of formula (I). For example, a substituent containing hydroxyl could be coupled to a carrier which renders the compound biologically inactive until it is removed by endogenous enzymes or, for example, by enzymes targeted to a particular receptor or location in the subject.

A compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglycamine. A compound of formula (I) can be treated with an acid to form acid addition salts. Examples of such acids include hydrochloric acid, hydrobromic acid, hydroiodic acid, sulfuric acid, methanesulfonic acid, phosphoric acid, p-bromophenylsulfonic acid, carbonic acid, succinic acid, citric acid, benzoic acid, oxalic acid, malonic acid, salicylic acid, malic acid, fumaric acid, ascorbic acid, maleic acid, acetic acid, and other mineral and organic acids well known to those skilled in the art. The acid addition salts can be prepared by treating a compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute aqueous basic solution (e.g., sodium hydroxide, sodium bicarbonate, potassium carbonate, or ammonia).

Some of the compounds of this invention may be crystallized or recrystallized from solvents such as aqueous and organic solvents. In such cases solvates may be formed. This invention includes within its scope stoichiometric solvates including hydrates as well as compounds containing variable amounts of water that may be produced by processes such as lyophilization.

Compounds of formula (I) may contain one or more asymmetric centers and thus can exist as enantiomers or diastereomers. It is to be understood that the invention includes both mixtures and separate individual isomers of compounds of the formula (I). Furthermore, certain compounds of the formula (I) which contain alkenyl groups may exist as cis- or trans-isomers. In each instance, the invention includes both mixtures and separate individual isomers.

Compounds of formula (I) may also exist in tautomeric forms and the invention includes both mixtures and separate individual tautomers thereof.

Also included in the invention are radiolabelled derivatives of compounds of formula (I) which are suitable for biological studies.

As used herein, the term "alkyl" group refers to a saturated aliphatic hydrocarbon group containing 1-10 (e.g., 1-6 or 1-4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as alkoxy, cycloalkoxy, amino, nitro, carboxy, cyano, halo, hydroxy, sulfo, or mercapto.

As used herein, the term "alkylene" group refers to a saturated aliphatic hydrocarbon group containing 1-10 (e.g., 1-6 or 1-4) carbon atoms. An alkylene group can be straight or branched. Examples of an alkylene group include, but are not limited to, methylene, ethylene, propylene, isopropylene, butylene, isobutylene, sec-butylene, tert-butylene, n-pentylene, n-heptylene, and 2-ethylhexylene. An alkylene group can be optionally substituted with one or more substituents such as alkoxy, cycloalkoxy, amino, nitro, carboxy, cyano, halo, hydroxy, sulfo, or mercapto.

As used herein, the term "alkenylene" group refers to an aliphatic carbon group that contains 2-10 (e.g., 2-6 or 2-4) carbon atoms and at least one double bond. Like an alkylene group, an alkenylene group can be straight or branched. Examples of an alkenylene group include, but are not limited to, allylene, isoprenylene, 2-butenylene, and 2-hexenylene. An alkenylene group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkylalkylcarbonylamino, arylcarbonylamino, aralkylcarbonylamino, heterocycloalkylcarbonylamino, heterocycloalkylalkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, the term "alkynylene" group refers to an aliphatic carbon group that contains 2-10 (e.g., 2-6 or 2-4) carbon atoms and has at least one triple bond. An alkynylene group can be straight or branched. Examples of an alkynylene group include, but are not limited to, propargylene and butynylene. An alkynylene group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkylalkylcarbonylamino, arylcarbonylamino, aralkylcarbonylamino, heterocycloalkylcarbonylamino, heterocycloalkylalkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, the term "cycloalkyl" group refers to an aliphatic carbocyclic ring of 3-10 (e.g., 4-8) carbon atoms. Examples of cycloalkyl groups include cyclopropyl, cyclopentyl, cyclohexyl, cycloheptyl, adamantly, norbornyl, cubyl, octahydroindenyl, decahydronaphthyl; bicyclo[3.2.1]octyl, bicyclo[2.2.2]octyl, bicyclo[3.3.1]nonyl, and bicyclo[3.2.3]nonyl.

As used herein, the term "alkoxy" group refers to an alkyl-O-group where "alkyl" has been defined previously.

As used herein, the term "haloalkyl" group refers to an alkyl group containing one or more halogen atoms. Examples of haloalkyl groups include fluoromethyl, chloromethyl, bromomethyl, and trifluoromethyl.

As used herein, the term "halogen" or "halo" group refers to fluorine, chlorine, bromine or iodine.

As used herein, the term "ALK5 and/or ALK4 inhibitor" refers to a compound, other than inhibitory Smads, e.g. Smad6 and Smad7, which selectively inhibits the ALK5 and/or ALK4 receptors preferentially over p38 or type II receptors.

As used herein, the term "ALK5- and/or ALK4-mediated disease state" refers to any disease state which is mediated (or modulated) by ALK5 and/or ALK4, for example, a disease which is modulated by the inhibition of the phosphorylation of Smad2 and Smad3 in the TGF-β and/or activin signaling pathways.

As used herein, the term "ulcers" is used to include, but not to be limited to, diabetic ulcers, chronic ulcers, gastric ulcers, and duodenal ulcers.

Compounds of formula (I) may be prepared by a number of known methods from commercially available or known starting materials. If the starting materials are unavailable from a commercial source, they can be prepared by procedures known in the art.

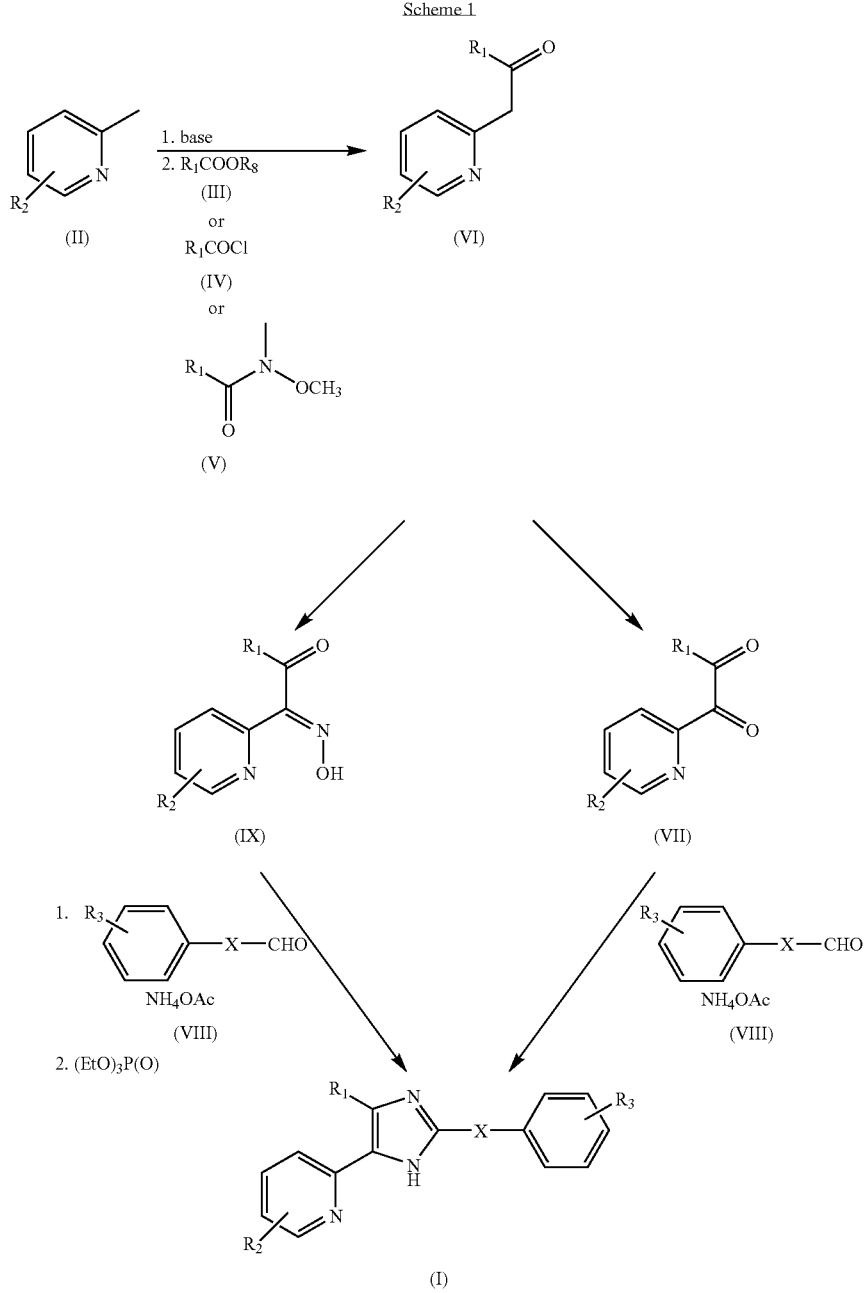

In one method, compounds of formula (I) wherein $A_1$ is N and $A_2$ is NH, or $A_1$ is NH and $A_2$ is N are prepared according to Scheme 1. Specifically, optionally substituted 2-methylpyridine (II) is deprotonated by a base such as LDA or LiHMDS before reacting with (III) wherein $R_8$ is $C_{1-6}$alkyl, $R_1$COCl (IV), or $R_1$-substituted carboxylic acid methoxy-methyl-amide (V) to form a ketone (VI). The methoxy-methyl-amide (V) can be prepared by reacting a corresponding acid chloride (IV) with N,O-dimethylhydroxylamine hydrochloride. The ketone (VI) may be oxidized to a diketone (VII) with HBr in DMSO. This diketone (VII) can then be condensed with an appropriately substituted aldehyde (VIII) or protected aldehyde derivative in the presence of ammonium acetate to yield a compound of formula (I). $R_1$, $R_2$, $R_3$, and X have been defined as above. The aldehyde (VIII) can be prepared according to the methods outlined in WO 02/096875 A1 and Liquid Crystals 10:273-287 (1991). Alternatively, the ketone (VI) can be treated with sodium nitrite in HCl or acetic acid to afford an α-keto-oxime (IX), which can be then condensed with an appropriately substituted aldehyde (VIII) or protected aldehyde derivative in the presence of ammonium acetate to give the N-hydroxyimidazoles. Treatment of this with triethylphophite affords a compound of formula (I).

In another method, when $R_3$ in compounds of formula (I) is $-(CH_2)_p-CN$ or $-(CH_2)_p-CH=CH-CN$, it can be further functionalized to form a compound of formula (I) as depicted in Scheme 2. $R_1$, $R_2$, X and P have been defined as above and $R_4$ and $R_5$ are independently H or $C_{1-6}$alkyl.

Scheme 2

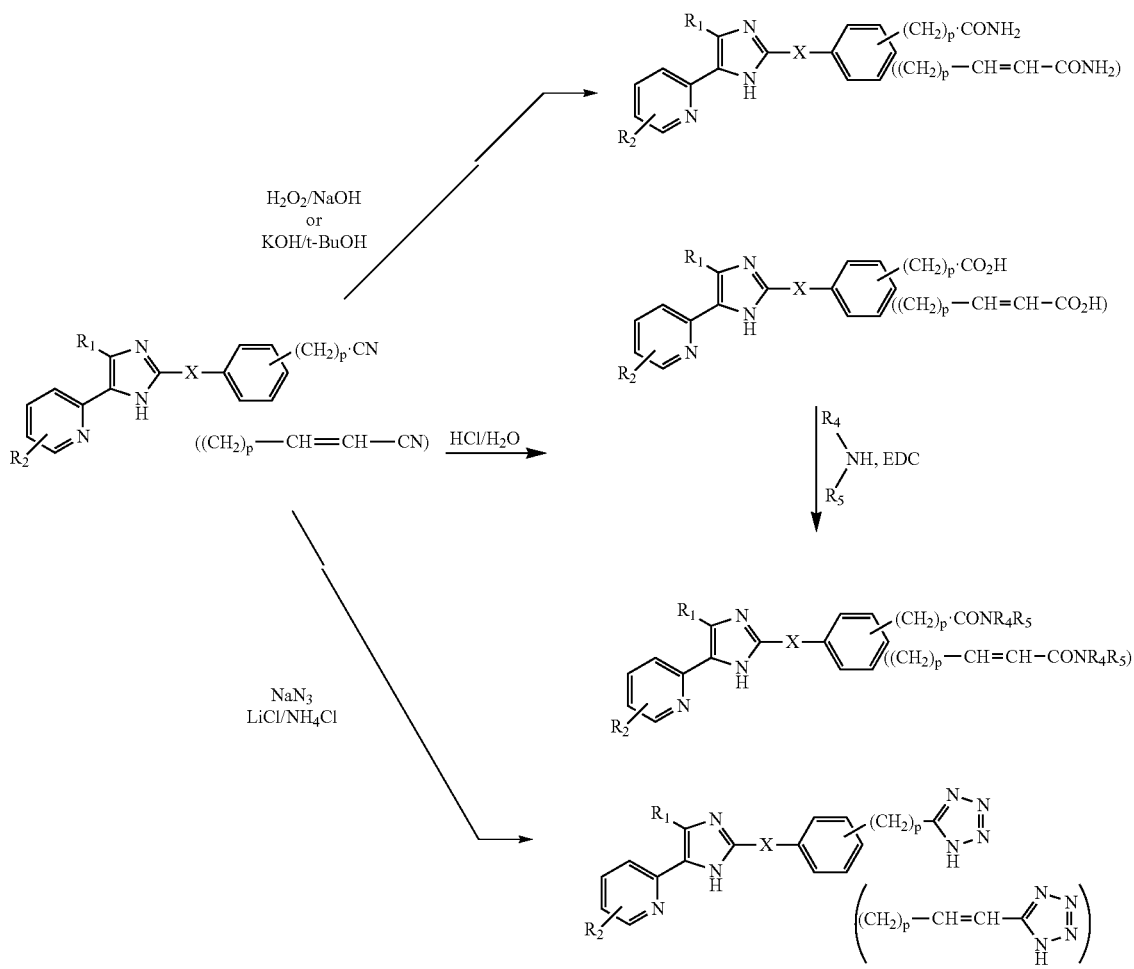

The resulting compounds of this invention represented by the formula (I)-(IX), for example, can be separated and purified by appropriate conventional methods such as column chromatography and recrystallization.

Compounds of the invention may be administered by any suitable route, for example by oral, buccal, sub-lingual, rectal, vaginal, nasal, topical or parenteral (including intravenous, intramuscular, subcutaneous and intracoronary) administration.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually, they will form up to about 80% of the formulation.

For administration to humans in the curative or prophylactic treatment of the disorders identified above, oral, buccal or sub-lingual dosages of a compound of formula (I) will generally be in the range of from 50-5000 mg daily for an average adult patient (70 kg). Thus for a typical adult patient, individual tablets or capsules contain from 25-500 mg of active compound, in a suitable pharmaceutically acceptable vehicle or carrier, for administration in single or multiple doses, once or several times per day. Dosages for parenteral administration will typically be within the range of from 25-250 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, a compound of formula (I) can be administered alone, but will generally be administered in admixture with a pharmaceutical carrier selected with regard to the intended route of administration and standard pharmaceutical practice. For example, the compound may be administered orally, buccally or sublingually, in the form of tablets containing excipients such as starch or lactose, or in capsules or ovules either alone or in admixture with excipients, or in the form of elixirs or suspensions containing flavoring or coloring agents. Such liquid preparations may be prepared with pharmaceutically acceptable additives such as suspending agent (e.g. methylcellulose, a semi-synthetic glyceride such as witepsol or mixtures of glycerides such as a mixture of apricot kernel oil and PEG-6 esters or mixtures of PEG-8 and caprylic/capric glycerides). A compound may also be injected parenterally, for example intravenously, intramuscularly, subcutaneously or intracoronarily. For parenteral administration, the compound is best used in the form of a sterile aqueous solution which may contain other substances, for example, salts, or monosaccharides such as mannitol or glucose, to make the solution isotonic with blood.

Thus, the present invention provides in a further aspect a pharmaceutical composition comprising a compound of formula (I), or a pharmaceutically acceptable salt or solvate thereof, together with a pharmaceutically acceptable diluent or carrier therefor.

The present invention also provides a compound of formula (I), or a pharmaceutically acceptable salt or solvate thereof, or a pharmaceutical composition containing either entity, for use in therapy.

The present invention further provides the use of a compound of formula (I), or a pharmaceutically acceptable salt or solvate thereof, or a pharmaceutical composition containing either entity, for the manufacture of a medicament for the treatment of a disease, mediated by the ALK5 and/or ALK4 receptors in mammals.

ALK5- and/or ALK4-mediated disease states include, but are not limited to, glomerulonephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, acute lung injury, adult respiratory distress syndrome, idiopathic pulmonary fibrosis, chronic obstructive pulmonary disease, pulmonary fibrosis due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Alzheimer's disease, Raynaud's syndrome, fibrotic cancers, tumor metastasis growth, radiation-induced fibrosis, and thrombosis.

The invention further provides a method of inhibiting the TGF-β and/or activin signaling pathways in mammals, for example, inhibiting the phosphorylation of Smad2 or Smad3 by ALK5 and/or ALK4.

The invention further provides a method of reducing the accumulation of excess extracellular matrix in mammals by inhibiting the TGF-β and/or activin signaling pathways, for example, inhibiting the phosphorylation of Smad2 or Smad3 by ALK5 and/or ALK4.

The invention further provides a method of inhibiting metastasis of tumor cells in mammals by inhibiting the TGF-β signaling pathway.

The invention further provides a method of treating carcinomas mediated by an overexpression of TGF-β in mammals by inhibiting the TGF-β signaling pathway. The present invention is further illustrated in the following Examples, which are not intended to limit the scope of the invention. In the Examples, electrospray ionization mass spectra (ESI-MS) were obtained on a Q-T of 2 mass spectrometer (Micromass, Manchester, UK).

EXAMPLES

Practice Example 1

Preparation of 3-((4-(benzo[1,3]dioxol-5-yl)-5-(6-methylpyridin-2-yl)-1(3)H-imidazol-2-yl)methyl)benzonitrile Example 5

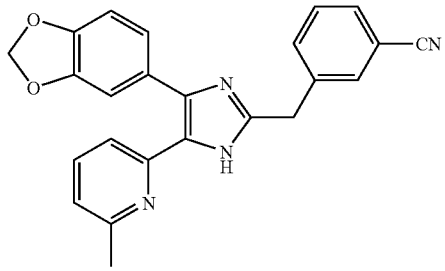 [SMILES: Cc1cccc(-c2[nH]c(Cc3cccc(C#N)c3)nc2-c2ccc3c(c2)OCO3)n1]

To a stirred solution of 1-(benzo[1,3]dioxol-5-yl)-2-(6-methylpyridin-2-yl)ethane-1,2-dione (50 mg, 0.19 mmol) (prepared according to the method described in WO 01/62756 A1) in AcOH (3 mL) were added 3-(formylmethyl)benzonitrile (28 mg, 0.19 mmol) (prepared according to the method described in WO 02/096875 A1) and NH$_4$OAc (86 mg, 1.11 mmol), and the mixture was heated at 120° C. for 3 h. The pH of the cooled reaction mixture was adjusted to pH 7-8 at 0° C. with 28% NH$_4$OH, and the reaction mixture was extracted with CH$_2$Cl$_2$ (10 mL). The CH$_2$Cl$_2$ solution was washed with water (5 mL) and brine (5 mL), dried (anhydrous Na$_2$SO$_4$), filtered, and evaporated to dryness under reduced pressure. The residue was purified by MPLC on silica gel using a mixture of MeOH and CH$_2$Cl$_2$ (1:19 (v/v)) as eluent to give 26 mg (36%) of 3-((4-benzo[1,3]dioxol-5-yl)-5-(6-methylpyridin-2-yl)-1(3)H-imidazol-2-yl)methyl)benzonitrile as a solid. MS (ESI) m/z 395.13 (MH$^+$). $^1$H NMR (400 MHz, CDCl$_3$) δ 7.52 (s, 1H), 7.46 (m, 1H), 7.40 (t, 1H), 7.33 (d, 1H), 7.32-7.26 (m, 2H), 7.09-7.04 (m, 2H), 6.90 (d, 1H), 6.82 (d, 1H), 5.96 (s, 2H), 4.10 (s, 2H), 2.38 (s, 3H).

Practice Example 2

Preparation of 3-((4-(benzo[1,3]dioxol-5-yl)-5-(6-methylpyridin-2-yl)-1(3)H-imidazol-2-yl)methyl)benzamide Example 6

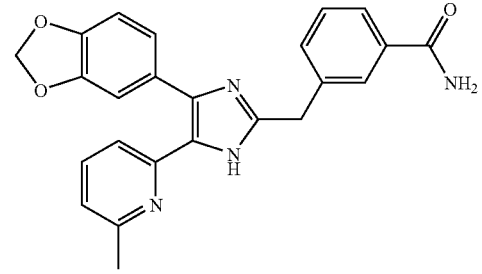 [SMILES: Cc1cccc(-c2[nH]c(Cc3cccc(C(N)=O)c3)nc2-c2ccc3c(c2)OCO3)n1]

To a stirred solution of 3-((4-(benzo[1,3]dioxol-5-yl)-5-(6-methylpyridin-2-yl)-1(3)H-imidazol-2-yl)methyl)benzonitrile (70 mg, 0.17 mmol) in EtOH (4 mL) at room temperature were added 30% H$_2$O$_2$ (0.59 mmol) and 6 N NaOH (0.04 mmol) solution. The mixture was warmed to 50-60° C. and stirred for 3 h, and to it, 1 N HCl solution was added to adjust to pH 7-8 at 0° C. The ethanol solvent was evaporated off under reduced pressure, and the residue was dissolved in $CH_2Cl_2$ (30 mL). The $CH_2Cl_2$ solution was washed with water (15 mL) and brine (15 mL), dried (anhydrous $Na_2SO_4$), filtered, and evaporated to dryness under reduced pressure. The residue was purified by MPLC on silica gel using a mixture of MeOH and $CH_2Cl_2$ (1:9 (v/v)) as eluent to give 23 mg (33%) of 3-((4-benzo[1,3]dioxol-5-yl)-5-(6-methylpyridin-2-yl)-1(3)H-imidazol-2-yl)methyl)benzamide as a solid. MS (ESI) m/z 413.11 (MH$^+$). $^1$H NMR (400 MHz, CDCl$_3$) δ 7.59 (s, 1H), 7.52 (d, 1H), 7.37 (dd, 1H), 7.24 (m, 2H), 7.15 (t, 1H), 7.01 (overlapped, 1H), 7.00 (s, 1H), 6.88 (d, 1H), 6.75 (d, 1H), 6.70 (br s, 1H), 6.02 (br s, 1H), 5.92 (s, 2H), 4.00 (s, 2H), 2.34 (s, 3H).

Practice Example 3

Preparation of 4-(3-(4-(benzo[1,3]dioxol-5-yl)-5-(6-methylpyridin-2-yl)-1(3)H-imidazol-2-yl)propyl)benzonitrile Example 13

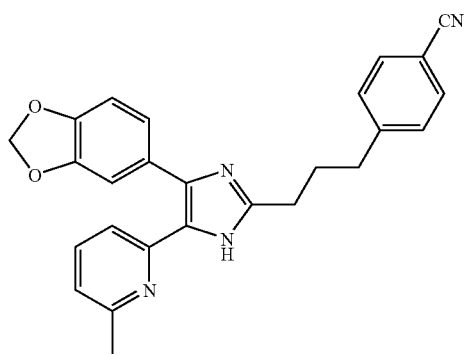 [SMILES: Cc1cccc(-c2[nH]c(CCCc3ccc(C#N)cc3)nc2-c2ccc3c(c2)OCO3)n1]

To a stirred solution of 1-(benzo[1,3]dioxol-5-yl)-2-(6-methylpyridin-2-yl)ethane-1,2-dione (230 mg, 0.86 mmol) in AcOH (8 mL) were added 4-(3-formylpropyl)benzonitrile (156 mg, 0.90 mmol) (prepared according to the method described in Kelly, S. M., *Liquid Crystals* 10: 273-287 (1991)) and NH$_4$OAc (396 mg, 5.14 mmol), and the mixture was heated at 120° for 3 h. The pH of the cooled reaction mixture was adjusted to pH 7-8 at 0° C. with 28% NH$_4$OH, and the reaction mixture was extracted with $CH_2Cl_2$ (3×30 mL). The combined $CH_2Cl_2$ solution was dried (anhydrous Na$_2$SO$_4$), filtered, and evaporated to dryness under reduced pressure. The residue was purified by MPLC on silica gel using a mixture of MeOH and $CH_2Cl_2$ (1:30, then (v/v)) as eluent to give 130 mg (36%) of 4-(3-(4-(benzo[1,3]dioxol-5-yl)-5-(6-methylpyridin-2-yl)-1(3)H-imidazol-2-yl)propyl)benzonitrile as a solid. MS (ESI) m/z 423.14. $^1$H NMR (400 MHz, CDCl$_3$) δ 10.63 (br s, 1H), 7.51 (d, 2H), 7.42 (dd, 1H), 7.30 (d, 1H), 7.24 (d, 2H), 7.10-7.04 (m, 2H), 6.93 (d, 1H), 6.82 (d, 1H), 5.98 (s, 2H), 2.74 (m, 4H), 2.47 (s, 3H), 2.07 (m, 2H).

The compounds listed in the following Table 1 were prepared in an analogous manner to those described in the Practice Examples 1-3 above. The mass spectroscopy data of these compounds are included in Table 1 below.

TABLE 1

| Example | Structure | $^1$H NMR | MS (ESI) m/z (MH$^+$) |
| --- | --- | --- | --- |
| 1 | 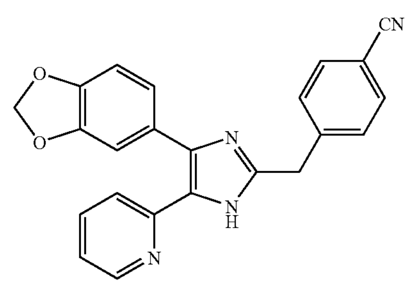 [SMILES: N#Cc1ccc(Cc2nc(-c3ccc4c(c3)OCO4)c(-c3ccccn3)[nH]2)cc1] | (400 MHz, CDCl$_3$) δ 11.20 (br s, 1 H), 8.36 (d, 1 H), 7.50 (m, 2 H), 7.44 (d, 2 H), 7.27 (d, 2 H), 7.08-7.02 (m, 3 H), 6.82 (d, 1 H), 5.97 (s, 2 H), 4.10 (s, 2 H) | 381.11 |
| 2 | 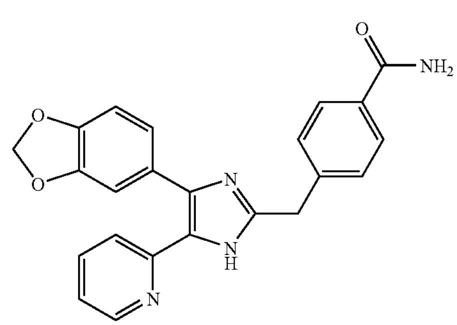 [SMILES: NC(=O)c1ccc(Cc2nc(-c3ccc4c(c3)OCO4)c(-c3ccccn3)[nH]2)cc1] | (400 MHz, CDCl$_3$) δ 11.70 (br s, 1 H), 8.33 (d, 1 H), 7.49 (m, 2 H), 7.47 (d, 2 H), 7.14 (d, 2 H), 7.08-7.00 (m, 3 H), 6.80 (d, 1 H), 6.38 (br s, 1 H), 5.96 (s, 2 H), 5.90 (br s, 1 H), 4.06 (s, 2 H) | 399.12 |

TABLE 1-continued

| Example | Structure | ¹H NMR | MS (ESI) m/z (MH⁺) |
|---|---|---|---|
| 3 | 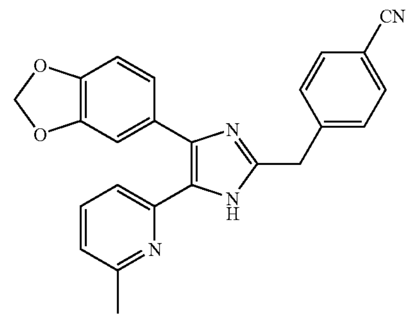 [SMILES: Cc1cccc(-c2[nH]c(Cc3ccc(C#N)cc3)nc2-c2ccc3c(c2)OCO3)n1] | (400 MHz, CDCl₃) δ 11.40 (br s, 1 H), 7.45 (d, 2 H), 7.44 (overlapped, 1 H), 7.33 (d, 1 H), 7.25 (d, 2 H), 7.10 (d, 1 H), 7.07 (s, 1 H), 6.93 (d, 1 H), 6.84 (d, 1 H), 6.00 (s, 2 H), 4.09 (s, 2 H), 2.34 (s, 3 H) | 395.13 |
| 4 | 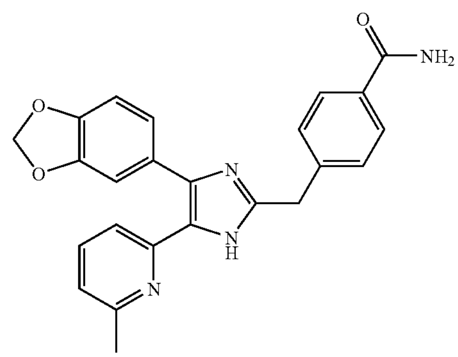 [SMILES: Cc1cccc(-c2[nH]c(Cc3ccc(C(N)=O)cc3)nc2-c2ccc3c(c2)OCO3)n1] | (400 MHz, CDCl₃) δ 11.70 (br s, 1 H), 7.45 (d, 2 H), 7.39 (dd, 1 H), 7.27 (d, 1 H), 7.10 (d, 2 H), 7.06 (overlapped, 1 H), 7.05 (s, 1 H), 6.87 (d, 1 H), 6.80 (d, 1 H), 6.39 (br s, 1 H), 5.95 (s, 2 H), 5.78 (br s, 1 H), 4.02 (s, 2 H), 2.27 (s, 3 H) | 413.11 |
| 5 | 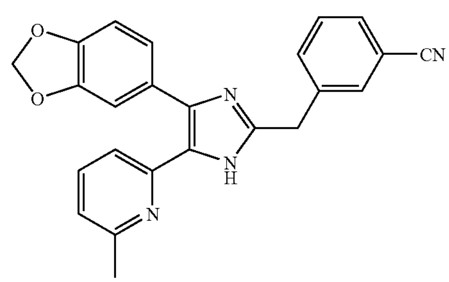 [SMILES: Cc1cccc(-c2[nH]c(Cc3cccc(C#N)c3)nc2-c2ccc3c(c2)OCO3)n1] | (400 MHz, CDCl₃) δ 7.52 (s, 1 H), 7.46 (m, 1 H), 7.40 (t, 1 H), 7.33 (d, 1 H), 7.32-7.26 (m, 2 H), 7.09-7.04 (m, 2 H), 6.90 (d, 1 H), 6.82 (d, 1 H), 5.96 (s, 2 H), 4.10 (s, 2 H), 2.38 (s, 3 H) | 395.13 |
| 6 | 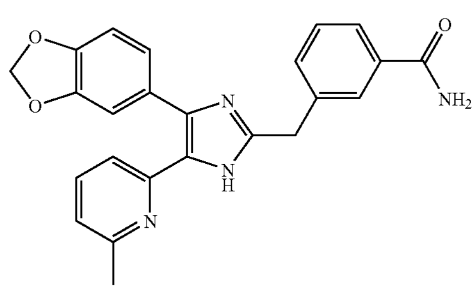 [SMILES: Cc1cccc(-c2[nH]c(Cc3cccc(C(N)=O)c3)nc2-c2ccc3c(c2)OCO3)n1] | (400 MHz, CDCl₃) δ 7.59 (s, 1 H), 7.52 (d, 1 H), 7.37 (dd, 1 H), 7.24 (m, 2 H), 7.15 (t, 1 H), 7.01 (overlapped, 1 H), 7.00 (s, 1 H), 6.88 (d, 1 H), 6.75 (d, 1 H), 6.70 (br s, 1 H), 6.02 (br s, 1 H), 5.92 (s, 2 H), 4.00 (s, 2 H), 2.34 (s, 3 H) | 413.11 |
| 7 | 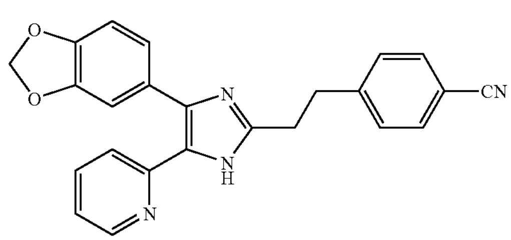 [SMILES: N#Cc1ccc(CCc2nc(-c3ccc4c(c3)OCO4)c(-c3ccccn3)[nH]2)cc1] | (400 MHz, CDCl₃) δ 10.22 (br s, 1 H), 8.47 (d, 1 H), 7.58 (dd, 2 H), 7.52 (m, 2 H), 7.32 (d, 2 H), 7.13-7.03 (m, 3 H), 6.86 (d, 2 H), 6.01 (s, 2 H), 3.19 (m, 2 H), 3.07 (m, 2 H) | 395.12 |

TABLE 1-continued

| Example | Structure | ¹H NMR | MS (ESI) m/z (MH⁺) |
|---|---|---|---|
| 8 | 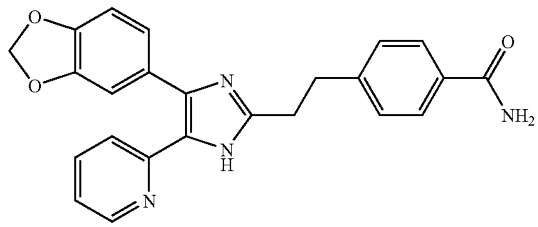 [SMILES: NC(=O)c1ccc(CCc2nc(-c3ccc4c(c3)OCO4)c(-c3ccccn3)[nH]2)cc1] | (400 MHz, CD₃OD) δ 8.51 (m, 1 H), 7.80 (d, 2 H), 7.70 (ddd, 1 H), 7.43 (d, 1 H), 7.34 (d, 2 H), 7.23 (m, 1 H), 6.92 (dd, 1 H), 6.89 (d, 1 H), 6.83 (d, 1 H), 5.97 (s, 2 H), 3.15 (m, 2 H), 3.09 (m, 2 H) | 413.15 |
| 9 | 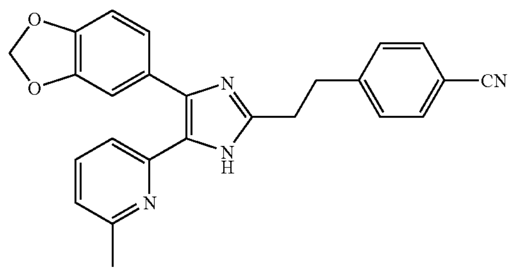 [SMILES: Cc1cccc(-c2[nH]c(CCc3ccc(C#N)cc3)nc2-c2ccc3c(c2)OCO3)n1] | (400 MHz, CDCl₃) δ 10.53 (br s, 1 H), 7.56 (d, 2 H), 7.43 (dd, 1 H), 7.31 (d, overlapped, 1 H), 7.29 (d, 2 H), 7.07 (d, 1 H), 7.04 (d, 1 H), 6.94 (d, 1 H), 6.84 (d, 1 H), 6.00 (s, 2 H), 3.13 (m, 2 H), 3.05 (m, 2 H), 2.48 (s, 3 H) | 409.13 |
| 10 | 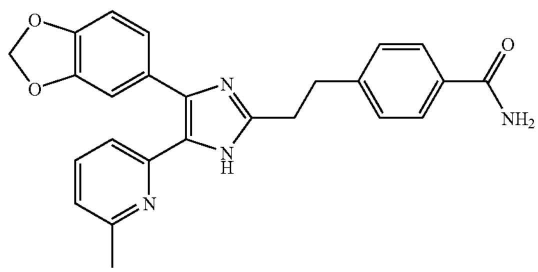 [SMILES: Cc1cccc(-c2[nH]c(CCc3ccc(C(N)=O)cc3)nc2-c2ccc3c(c2)OCO3)n1] | (400 MHz, CDCl₃) δ 10.85 (br s, 1 H), 7.66 (d, 2 H), 7.42 (t, 1 H), 7.30 (d, 1 H), 7.19 (d, 2 H), 7.07 (d, overlapped, 1 H), 7.05 (s, 1 H), 6.93 (d, 1 H), 6.82 (d, 1 H), 6.37 (br s, 1 H), 5.99 (s, 2 H), 5.69 (br s, 1 H), 3.04 (m, 2 H), 3.01 (m, 2 H), 2.45 (s, 3 H) | 427.10 |
| 11 | 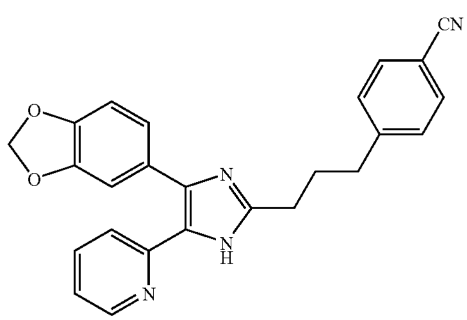 [SMILES: N#Cc1ccc(CCCc2nc(-c3ccc4c(c3)OCO4)c(-c3ccccn3)[nH]2)cc1] | (400 MHz, CDCl₃) δ 10.50 (br s, 1 H), 8.47 (d, 1 H), 7.57-7.47 (m, 4 H), 7.25 (d, 2 H), 7.10-7.03 (m, 3 H), 6.84 (d, 1 H), 5.99 (s, 2 H), 2.76 (m, 4 H), 2.10 (m, 2 H) | 409.13 |
| 12 | 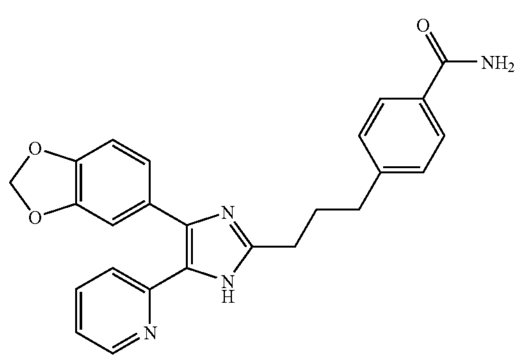 [SMILES: NC(=O)c1ccc(CCCc2nc(-c3ccc4c(c3)OCO4)c(-c3ccccn3)[nH]2)cc1] | (400 MHz, CDCl₃) δ 10.68 (br s, 1 H), 8.47 (d, 1 H), 7.68 (d, 2 H), 7.54-7.45 (m, 2 H), 7.21 (d, 2 H), 7.10-7.00 (m, 3 H), 6.83 (d, 1 H), 6.20 (br s, 1 H), 5.98 (s, 2 H), 2.75 (m, 4 H), 2.11 (m, 2 H) | 427.12 |

TABLE 1-continued

| Example | Structure | ¹H NMR | MS (ESI) m/z (MH⁺) |
|---|---|---|---|
| 13 | 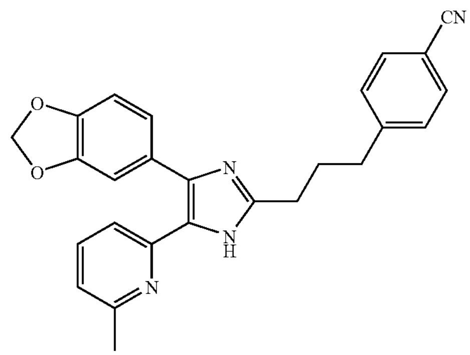 [SMILES: Cc1cccc(-c2[nH]c(CCCc3ccc(C#N)cc3)nc2-c2ccc3c(c2)OCO3)n1] | (400 MHz, CDCl₃) δ 10.63 (br s, 1 H), 7.51 (d, 2 H), 7.42 (dd, 1 H), 7.30 (d, 1 H), 7.24 (d, 2 H), 7.10-7.04 (m, 2 H), 6.93 (d, 1 H), 6.82 (d, 1 H), 5.98 (s, 2 H), 2.74 (m, 4 H), 2.47 (s, 3 H), 2.07 (m, 2 H) | 423.14 |
| 14 | 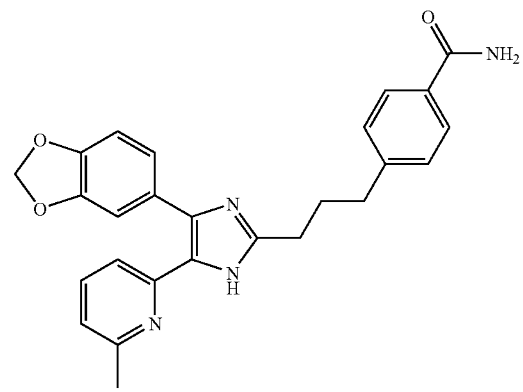 [SMILES: Cc1cccc(-c2[nH]c(CCCc3ccc(C(N)=O)cc3)nc2-c2ccc3c(c2)OCO3)n1] | (400 MHz, CDCl₃) δ 10.60 (br s, 1 H), 7.68 (d, 2 H), 7.41 (dd, 1 H), 7.30 (d, 1 H), 7.20 (d, 2 H), 7.10-7.05 (m, 2 H), 6.92 (d, 1 H), 6.82 (d, 1 H), 6.25 (br s, 1 H), 5.98 (s, 2 H), 5.75 (br s, 1 H), 2.73 (m, 4 H), 2.49 (s, 3 H), 2.07 (m, 2 H) | 441.12 |
| 15 | 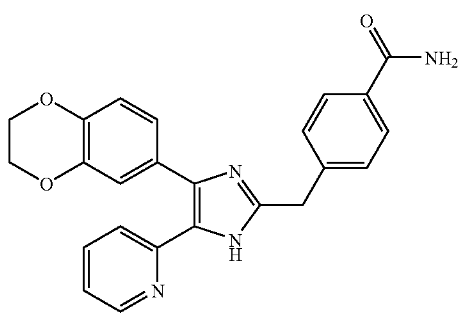 [SMILES: NC(=O)c1ccc(Cc2nc(-c3ccc4c(c3)OCCO4)c(-c3ccccn3)[nH]2)cc1] | (400 MHz, CDCl₃) δ 8.42 (d, 1 H), 7.71 (d, 2 H), 7.52 (m, 2 H), 7.36 (d, 2 H), 7.15 (d, 1 H), 7.10 (dd, 1 H), 7.05 (m, 1 H), 6.90 (d, 1 H), 6.12 (br s, 1 H), 5.59 (br s, 1 H), 4.29 (m, 4 H), 4.20 (s, 2 H) | 413.13 |
| 16 | 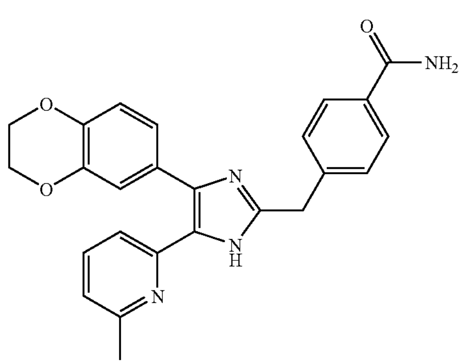 [SMILES: Cc1cccc(-c2[nH]c(Cc3ccc(C(N)=O)cc3)nc2-c2ccc3c(c2)OCCO3)n1] | (400 MHz, CDCl₃) δ 10.80 (br s, 1 H), 7.64 (d, 2 H), 7.41 (dd, 1 H), 7.34 (d, 1 H), 7.29 (d, 2 H), 7.15 (s, 1 H), 7.11 (d, 1 H), 6.90 (d, 1 H), 6.89 (d, 1 H), 6.20 (br s, 1 H), 5.55 (br s, 1 H), 4.29 (m, 4 H), 4.14 (s, 2 H), 2.38 (s, 3 H) | 427.19 |

TABLE 1-continued

| Example | Structure | ¹H NMR | MS (ESI) m/z (MH⁺) |
|---|---|---|---|
| 17 | 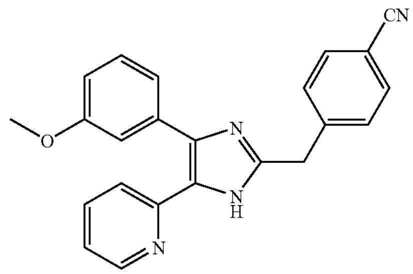 [SMILES: COc1cccc(-c2nc(Cc3ccc(C#N)cc3)[nH]c2-c2ccccn2)c1] | (400 MHz, CDCl₃) δ 11.07 (br s, 1 H), 8.41 (d, 1 H), 7.56-7.49 (m, 4 H), 7.35 (d, 2 H), 7.33 (overlapped, 1 H), 7.23-7.17 (m, 2 H), 7.08 (m, 1 H), 6.93 (m, 1 H), 4.17 (s, 2 H), 3.83 (s, 3 H) | 367.10 |
| 18 | 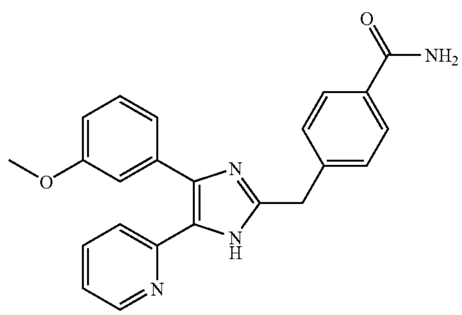 [SMILES: COc1cccc(-c2nc(Cc3ccc(C(N)=O)cc3)[nH]c2-c2ccccn2)c1] | (400 MHz, CDCl₃) δ 12.28 (br s, 1 H), 8.36 (d, 1 H), 7.57-7.49 (m, 2 H), 7.45 (d, 2 H), 7.29 (m, 1 H), 7.22-7.17 (m, 2 H), 7.11 (d, 2 H), 7.07 (m, 1 H), 6.89 (m, 1 H), 6.60 (br s, 1 H), 6.22 (br s, 1 H), 4.07 (s, 2 H), 3.78 (s, 3 H) | 385.08 |
| 19 | 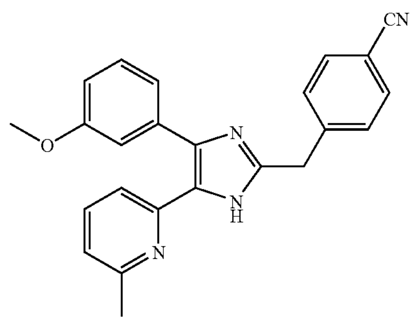 [SMILES: COc1cccc(-c2nc(Cc3ccc(C#N)cc3)[nH]c2-c2cccc(C)n2)c1] | (400 MHz, CDCl₃) δ 11.10 (br s, 1 H), 7.43 (d, 2 H), 7.35 (dd, 1 H), 7.30-7.18 (m, 4 H), 7.16-7.09 (m, 2 H), 6.89-6.81 (m, 2 H), 4.07 (s, 2 H), 3.74 (s, 3 H), 2.30 (s, 3 H) | 381.08 |
| 20 | 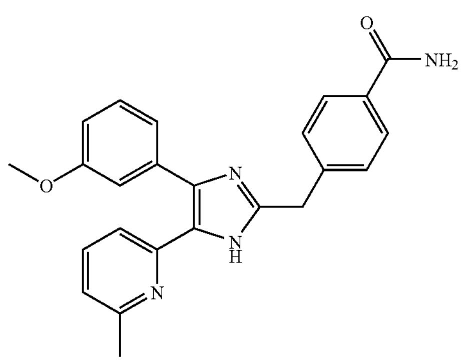 [SMILES: COc1cccc(-c2nc(Cc3ccc(C(N)=O)cc3)[nH]c2-c2cccc(C)n2)c1] | (400 MHz, CD₃OD) δ 7.80 (d, 2 H), 7.51 (m, 1 H), 7.41 (d, 2 H), 7.23 (m, 2 H), 7.10-7.01 (m, 3 H), 6.85 (d, 1 H), 4.17 (s, 2 H), 3.73 (s, 3 H), 2.50 (s, 3 H) | 399.11 |
| 21 | 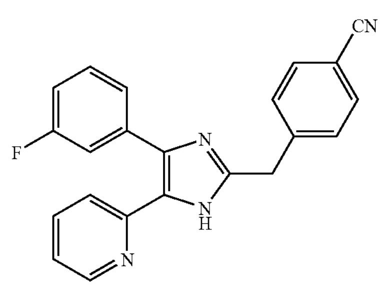 [SMILES: N#Cc1ccc(Cc2nc(-c3cccc(F)c3)c(-c3ccccn3)[nH]2)cc1] | (400 MHz, CDCl₃) δ 10.54 (br s, 1 H), 8.45 (d, 1 H), 7.58 (d, 2 H), 7.54 (m, 1 H), 7.48 (d, 1 H), 7.44-7.38 (m, 3 H), 7.38-7.33 (m, 2 H), 7.11 (m, 1 H), 7.05 (m, 1 H), 4.21 (s, 2 H) | 355.10 |

TABLE 1-continued

| Example | Structure | ¹H NMR | MS (ESI) m/z (MH⁺) |
|---|---|---|---|
| 22 | 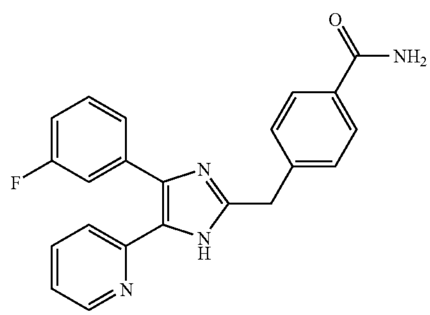 [SMILES: NC(=O)c1ccc(Cc2nc(-c3cccc(F)c3)c(-c3ccccn3)[nH]2)cc1] | (400 MHz, CDCl₃) δ 10.92 (br s, 1 H), 8.42 (d, 1 H), 7.64 (d, 2 H), 7.54 (m, 1 H), 7.47 (d, 1 H), 7.43 (d, 1 H), 7.40-7.34 (m, 2 H), 7.30 (d, 2 H), 7.12-7.03 (m, 2 H), 6.15 (br s, 1 H), 5.82 (br s, 1 H), 4.19 (s, 2 H) | 373.11 |
| 23 | 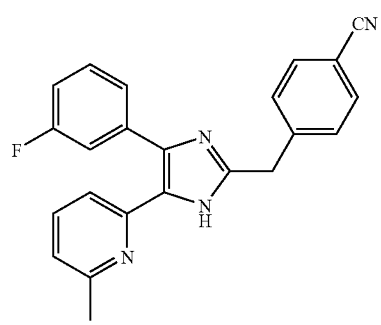 [SMILES: Cc1cccc(-c2[nH]c(Cc3ccc(C#N)cc3)nc2-c2cccc(F)c2)n1] | (400 MHz, CDCl₃) δ 10.27 (br s, 1 H), 7.60 (d, 2 H), 7.46-7.40 (overlapped, 2 H), 7.42 (d, 2 H), 7.36 (m, 2 H), 7.29 (d, 1 H), 7.05 (m, 1 H), 6.97 (d, 1 H), 4.22 (s, 2 H), 2.48 (s, 3 H) | 369.11 |
| 24 | 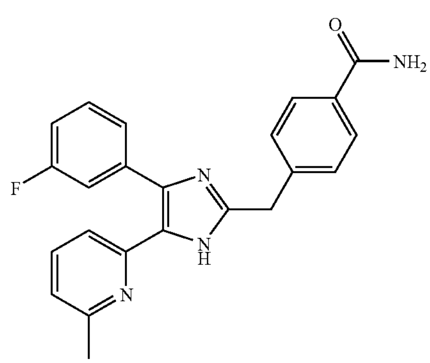 [SMILES: Cc1cccc(-c2[nH]c(Cc3ccc(C(N)=O)cc3)nc2-c2cccc(F)c2)n1] | (400 MHz, CDCl₃) δ 10.94 (br s, 1 H), 7.63 (d, 2 H), 7.46-7.40 (m, 2 H), 7.40-7.32 (m, 2 H), 7.29 (overlapped, 1 H), 7.28 (d, 2 H), 7.04 (m, 1 H), 6.94 (d, 1 H), 6.16 (br s, 1 H), 5.71 (br s, 1 H), 4.16 (s, 2 H), 2.40 (s, 3 H) | 387.19 |
| 25 | 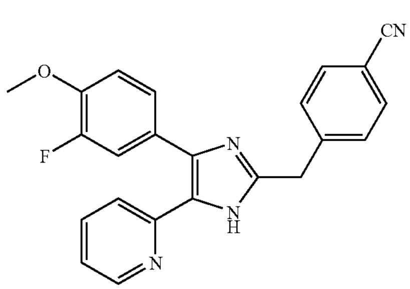 [SMILES: COc1ccc(-c2nc(Cc3ccc(C#N)cc3)[nH]c2-c2ccccn2)cc1F] | (400 MHz, CDCl₃) δ 10.47 (br s, 1 H), 8.44 (d, 1 H), 7.57 (d, 2 H), 7.53 (d, 1 H), 7.48 (d, 1 H), 7.39 (d, 2 H), 7.36 (overlapped, 2 H), 7.09 (dd, 1 H), 7.01 (t, 1 H), 4.19 (s, 2 H), 3.94 (s, 3 H) | 385.13 |

TABLE 1-continued

| Example | Structure | ¹H NMR | MS (ESI) m/z (MH⁺) |
|---|---|---|---|
| 26 | 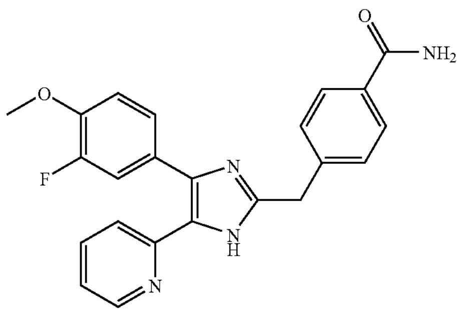 [SMILES: COc1ccc(-c2nc(Cc3ccc(C(N)=O)cc3)[nH]c2-c2ccccn2)cc1F] | (400 MHz, CDCl₃) δ 10.94 (br s, 1 H), 8.40 (d, 1 H), 7.62 (d, 2 H), 7.53 (m, 1 H), 7.47 (d, 1 H), 7.41-7.35 (m, 2 H), 7.29 (d, 2 H), 7.08 (m, 1 H), 7.00 (dd, 1 H), 6.18 (br s, 1 H), 5.84 (br s, 1 H), 4.17 (s, 2 H), 3.94 (s, 3 H) | 403.18 |
| 27 | 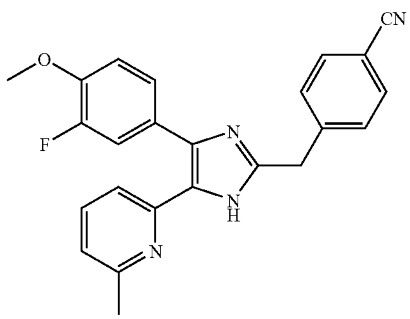 [SMILES: COc1ccc(-c2nc(Cc3ccc(C#N)cc3)[nH]c2-c2cccc(C)n2)cc1F] | (400 MHz, CDCl₃) δ 10.25 (br s, 1 H), 7.59 (d, 2 H), 7.41 (d, 2 H), 7.47-7.34 (overlapped, 3 H), 7.29 (d, 1 H), 7.00 (t, 1 H), 6.95 (d, 1 H), 4.20 (s, 2 H), 3.94 (s, 3 H), 2.47 (s, 3 H) | 399.15 |
| 28 | 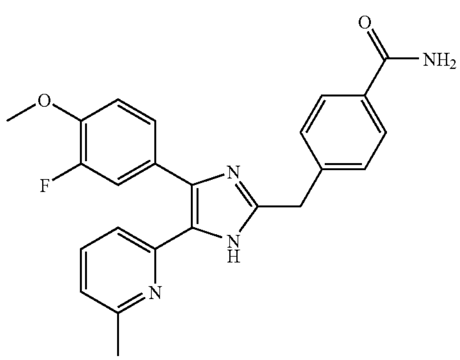 [SMILES: COc1ccc(-c2nc(Cc3ccc(C(N)=O)cc3)[nH]c2-c2cccc(C)n2)cc1F] | (400 MHz, CDCl₃) δ 10.97 (br s, 1 H), 7.61 (d, 2 H), 7.45-7.34 (m, 3 H), 7.30-7.24 (m, 3 H), 6.99 (dd, 1 H), 6.93 (d, 1 H), 6.20 (br s, 1 H), 5.70 (br s, 1 H), 4.14 (s, 2 H), 3.93 (s, 3 H), 2.39 (s, 3 H) | 417.15 |

Biological Data

The biological activity of the compounds of the invention may be assessed using the following assays:

Cell-Free Assay for Evalutating Inhibition of ALK5 Kinase Phosphorylation of Smad3

The His-tagged, constitutively active ALK5 (T204D) and Smad3 full protein were expressed in insect cells using the Invitrogen BacNBlue baculovirus expression system. Expressed proteins were purified with Qiagen Ni-NTA resin column. The purified smad3 protein 200 ng was mixed with 100 µL of 0.1 M sodium bicarbonate coating buffer and coated into Flash-Plates by pipetting. Plates were covered and incubated at 4° C. for 16 hours. Then the plates were washed 3 times with 200 µL of coating buffer and allowed to block in 1% BSA in PBS at room temperature for 1 hour. The purified ALK5 protein 100 ng was mixed with 100 µL of reaction buffer containing 20 mM Tris-HCl (pH 7.4), 5 mM MgCl₂, 1 mM CaCl₂, 1 mM DTT, 1 µM ATP and 2 µCi γ-³²p-ATP, and 1 µL of each test compound of formula (I) prepared in 100% DMSO solution at different concentrations. The assay was then initiated with the addition of ALK5 reaction mixture into Smad3-coated Flash-Plates, followed by incubation at 30° C. for 3 hours. After incubation, the assay buffer was removed and washed 3 times with 200 µL of 10 mM sodium pyrophosphate solution. Then, the Flash-Plates were air-dried and counted on a Packard TopCount.

Compounds of formula (I) typically exhibited IC₅₀ values of less than 10 µM; some exhibited IC₅₀ values of less than 1 µM; and some even exhibited IC₅₀ values less than 50 nM.

Cell-Free Assay for Evaluating Inhibition of ALK4 Kinase Phosphorylation of Smad3

Inhibition of the ALK4 kinase phosphorylation of Smad3 by test compounds of formula (I) can be determined in a similar manner to that described above for ALK5 inhibition except that a similarly His-tagged ALK4 is used in place of the His-tagged, constitutively active ALK5.

Compounds of formula (I) typically exhibited IC₅₀ values of less than 10 µM; some exhibited IC₅₀ values of less than 1 µM.

Assay for Evaluating Cellular Inhibition of TGF-β Signaling

Biological activity of the compounds of formula (I) was determined by measuring their ability to inhibit TGF-β1-induced Smad binding element-luciferase (SBE-Luc) reporter activity and PAI-1-luciferase (p3TP-Lux) reporter activity in HepG2 cells. HepG2 cells were transiently transfected with either SBE-Luc reporter construct or p3TP-Lux reporter construct grown in DMEM medium containing 10% FBS, penicillin 100 U/mL, streptomycin 100 µg/mL, L-glutamine 2 mM, sodium pyruvate 1 mM, and non-essential amino acids. The transfected cells were then plated at a concentration of $2.5 \times 10^4$ cells/well in 96 well plates and starved for 3-6 hours in media with 0.5% FBS at 37° C. in a 5% $CO_2$ incubator. The cells were then stimulated with 5 ng/mL TGF-β1 ligand in the starvation media containing 1% DMSO either in the presence or absence of a test compound of formula (I) and incubated at 37° C. in a 5% $CO_2$ incubator for 24 hours. The media was washed out, and the luciferase activity in cell lysates was determined by using a luciferase assay system (Promega).

Compounds of formula (I) typically exhibited $IC_{50}$ values of less than 10 µM; some exhibited $IC_{50}$ values of less than 1 µM; and some even exhibited $IC_{50}$ values of less than 50 nM.

Having described the present invention, it will be apparent that many changes and modifications may be made to the above-described embodiments without departing from the spirit and the scope of the present invention.

What is claimed is:

1. A compound of formula (I) or a pharmaceutically acceptable salt thereof:

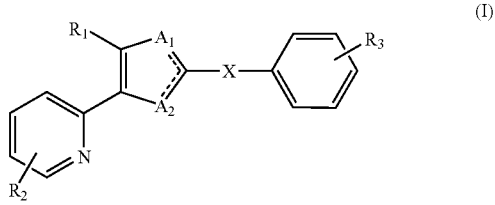

(I)

wherein $R_1$ is phenyl fused with a non-aromatic cyclic ring of 5 or 6 members wherein said cyclic ring optionally contains up to two oxygen atoms, or $R_1$ is phenyl substituted by one or more substituents selected from the group consisting of halo, OH and —O—$C_{1-6}$alkyl;
$R_2$ is H, OH, —O—$C_{1-6}$alkyl, —S—$C_{1-6}$alkyl, $C_{1-6}$alkyl, $C_{1-6}$haloalkyl, $NH_2$, or halo;
$R_3$ is H, $C_{1-6}$alkyl, $C_{3-7}$cycloalkyl, —$(CH_2)_p$—$NO_2$, —$(CH_2)_p$—$NR_4R_5$, —$(CH_2)_p$—CHO, —$(CH_2)_p$—CONHOH, —$(CH_2)_p$—CN, —$(CH_2)_p$—$CO_2H$, —$(CH_2)_p$—$CO_2R_4$, —$(CH_2)_p$—$CONR_4R_5$, —$(CH_2)_p$—tetrazole, —$(CH_2)_p$—$COR_4$, —$(CH_2)_q$—$(OR_6)_2$, —$(CH_2)_p$—$OR_4$, —$(CH_2)_p$—CH=CH—CN, —$(CH_2)_p$—CH=CH—$CO_2H$, —$(CH_2)_p$—CH=CH—$CO_2R_4$, —$(CH_2)_p$—CH=CH—$CONR_4R_5$, —$(CH_2)_p$—$NHCOR_4$, —$(CH_2)_p$—$NHCO_2R_4$, —$(CH_2)_p$—$CONHSO_2R_4$, —$(CH_2)_p$—$NHSO_2R_4$ or —$(CH_2)_p$—CH=CH-tetrazole;
$R_4$ and $R_5$ are independently H or $C_{1-6}$alkyl;
$R_6$ is $C_{1-6}$alkyl;
p is 0, 1, 2, 3, or 4;
q is 1, 2, 3, or 4;
X is $C_{1-10}$alkylene;
one of $A_1$ and $A_2$ is N and the other is $NR_7$; and
$R_7$ is H, or $C_{1-6}$alkyl.

2. The compound of claim 1, wherein $R_2$ is $C_1$-$C_6$ alkyl.
3. The compound of claim 2, wherein $R_2$ is methyl.
4. The compound of claim 1, wherein $R_1$ is benzo[1,3]dioxolyl, methoxyphenyl, fluorophenyl or phenyl substituted with fluoro and methoxy.
5. The compound of claim 1, wherein $R_3$ is CN.
6. The compound of claim 1, wherein $R_3$ is $CONR_4R_5$.
7. The compound according to claim 1, which is:
4-((4-(benzo[1,3]dioxol-5-yl)-5-(pyridin-2-yl)-1(3)H-imidazol-2-yl)methyl)benzonitrile;
4-((4-(benzo[1,3]dioxol-5-yl)-5-(pyridin-2-yl)-1(3)H-imidazol-2-yl)methyl)benzamide;
4-((4-(benzo[1,3]dioxol-5-yl)-5-(6-methylpyridin-2-yl)-1(3)H-imidazol-2-yl)methyl)benzonitrile;
4-((4-(benzo[1,3]dioxol-5-yl)-5-(6-methylpyridin-2-yl)-1(3)H-imidazol-2-yl)methyl)benzamide;
3-((4-(benzo[1,3]dioxol-5-yl)-5-(6-methylpyridin-2-yl)-1(3)H-imidazol-2-yl)methyl)benzonitrile;
3-((4-(benzo[1,3]dioxol-5-yl)-5-(6-methylpyridin-2-yl)-1(3)H-imidazol-2-yl)methyl)benzamide;
4-(2-(4-(benzo[1,3]dioxol-5-yl)-5-(pyridin-2-yl)-1(3)H-imidazol-2-yl)ethyl)benzonitrile;
4-(2-(4-(benzo[1,3]dioxol-5-yl)-5-(pyridin-2-yl)-1(3)H-imidazol-2-yl)ethyl)benzamide;
4-(2-(4-(benzo[1,3]dioxol-5-yl)-5-(6-methylpyridin-2-yl)-1(3)H-imidazol-2-yl)ethyl)benzonitrile;
4-(2-(4-(benzo[1,3]dioxol-5-yl)-5-(6-methylpyridin-2-yl)-1(3)H-imidazol-2-yl)ethyl)benzamide;
4-(3-(4-(benzo[1,3]dioxol-5-yl)-5-(pyridin-2-yl)-1(3)H-imidazol-2-yl)propyl)benzonitrile;
4-(3-(4-(benzo[1,3]dioxol-5-yl)-5-(pyridin-2-yl)-1(3)H-imidazol-2-yl)propyl)benzamide;
4-(3-(4-(benzo[1,3]dioxol-5-yl)-5-(6-methylpyridin-2-yl)-1(3)H-imidazol-2-yl)propyl)benzonitrile;
4-(3-(4-(benzo[1,3]dioxol-5-yl)-5-(6-methylpyridin-2-yl)-1(3)H-imidazol-2-yl)propyl)benzamide;
4-((4-(2,3,4a,8a-tetrahydrobenzo[b][1,4]dioxin-7-yl)-5-(pyridin-2-yl)-1(3)H-imidazol-2-yl)methyl)benzamide;
4-((4-(2,3,4a,8a-tetrahydrobenzo[b][1,4]dioxin-7-yl)-5-(6-methylpyridin-2-yl)-1(3)H-imidazol-2-yl)methyl)benzamide;
4-((4-(3-methoxyphenyl)-5-(pyridin-2-yl)-1H-imidazol-2-yl)methyl)benzonitrile;
4-((4-(3-methoxyphenyl)-5-(pyridin-2-yl)-1H-imidazol-2-yl)methyl)benzamide;
4-((4-(3-methoxyphenyl)-5-(6-methylpyridin-2-yl)-1H-imidazol-2-yl)methyl)benzonitrile;
4-((4-(3-methoxyphenyl)-5-(6-methylpyridin-2-yl)-1H-imidazol-2-yl)methyl)benzamide;
4-((4-(3-fluorophenyl)-5-(pyridine-2-yl)-1H-imidazol-2-yl)methyl)benzonitrile;
4-((4-(3-fluorophenyl)-5-(pyridin-2-yl)-1H-imidazol-2-yl)methyl)benzamide;
4-((4-(3-fluorophenyl)-5-(6-methylpyridin-2-yl)-1H-imidazol-2-yl)methyl)benzonitrile;
4-((4-(3-fluorophenyl)-5-(6-methylpyridin-2-yl)-1H-imidazol-2-yl)methyl)benzamide;
4-((4-(3-fluoro-4-methoxyphenyl)-5-(pyridin-2-yl)-1H-imidazol-2-yl)methyl)benzonitrile;
4-((4-(3-fluoro-4-methoxyphenyl)-5-(pyridin-2-yl)-1H-imidazol-2-yl)methyl)benzamide;
4-((4-(3-fluoro-4-methoxyphenyl)-5-(6-methylpyridin-2-yl)-1H-imidazol-2-yl)methyl)benzonitrile; or 4-((4-(3-fluoro-4-methoxyphenyl)-5-(6-methylpyridin-2-yl)-1H-imidazol-2-yl)methyl)benzamide,
or a pharmaceutically acceptable salt thereof.

8. A pharmaceutical composition comprising a compound of formula (I) as claimed in claim 1, or a pharmaceutically acceptable salt thereof, and a pharmaceutically acceptable diluent or carrier.

9. The pharmaceutical composition of claim 8, wherein the pharmaceutically acceptable salt is a salt of an acid selected from the group consisting of hydrochloric acid, hydrobromic acid, hydroiodic acid, sulfuric acid, methanesulfonic acid, phosphoric acid, p-bromophenylsulfonic acid, carbonic acid, succinic acid, citric acid, benzoic acid, oxalic acid, malonic acid, salicylic acid, malic acid, fumaric acid, ascorbic acid, maleic acid and acetic acid.

* * * * *